US00PP30506P2

(12) United States Plant Patent
Egger

(10) Patent No.: US PP30,506 P2
(45) Date of Patent: May 14, 2019

(54) ***AGASTACHE* PLANT NAMED 'TNAGAPO'**

(50) Latin Name: ***Agastache* hybrid**
Varietal Denomination: TNAGAPO

(71) Applicant: Terra Nova Nurseries, Inc., Canby, OR (US)

(72) Inventor: Janet N. Egger, Wilsonville, OR (US)

(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 15/998,098

(22) Filed: Jun. 29, 2018

(51) Int. Cl.
*A01H 5/02* (2018.01)

(52) U.S. Cl.
USPC ..... Plt./399

(58) Field of Classification Search
USPC ..... Plt./263.1, 399
See application file for complete search history.

*Primary Examiner* — Susan McCormick Ewoldt
*Assistant Examiner* — Karen M Redden
(74) *Attorney, Agent, or Firm* — Klarquist Sparkman, LLP

(57) ABSTRACT

A new and distinct form of *Agastache* plant characterized by clear orange flowers on numerous inflorescences, hardy and long lived, a long bloom time, a dense, bushy habit, and excellent vigor.

1 Drawing Sheet

Botanical denomination: *Agastache* hybrid.
Variety designation: 'TNAGAPO'.
Trademark designation: Poquito™ Orange

BACKGROUND OF THE INVENTION

The present invention relates to a new and distinct cultivar of *Agastache*, given the name, 'TNAGAPO'. *Agastache* is in the family Lamiaceae. This new variety is one of several selections of new *Agastache* using hardy and dwarf *Agastache* species in the breeding lines to provide hardiness and compactness. The new cultivar is a selection from the cross between the proprietary, unpatented seedlings *Agastache* 227-3, as the seed parent, and *Agastache* 205-3, as the pollen parent. The new cultivar was selected for its compact habit, hardiness, and orange flowers.

The trademark designation for the claimed plant is 'Poquito™ Orange'.

Compared to the seed parent, *Agastache* 227-3 the new cultivar is shorter and hardier with orange flowers rather than yellow.

Compared to the pollen parent, *Agastache* 205-3, the new cultivar is a more compact habit, with orange flowers rather than red.

Compared to *Agastache* 'Kudos Gold', (U.S. Plant Pat. No. 26,410) the new cultivar is shorter with orange flowers rather than gold.

This plant exhibits the following characteristics that make it unique:

1. clear orange flowers on numerous inflorescences,
2. hardy and long lived,
3. a long bloom time,
4. a dense, bushy habit, and
5. excellent vigor.

The new variety has been reproduced only by asexual propagation (stem cuttings and micropropagation using apical buds and nodes). Each of the progeny exhibits identical characteristics to the original plant. Asexual propagation by stem cuttings and micropropagation using apical buds and nodes as done in Canby, Oreg., shows that the foregoing characteristics and distinctions come true to form and are established and transmitted through succeeding propagations. The present invention has not been evaluated under all possible environmental conditions. The phenotype may vary with variations in environment without a change in the genotype of the plant.

BRIEF DESCRIPTION OF THE DRAWINGS

FIG. 1 shows a close up of the new cultivar *Agastache* 'TNAGAPO' as a two-year-old plant growing in the field in July in full sun in Canby, Oreg.

FIG. 2 shows the new cultivar *Agastache* 'TNAGAPO' as a two-year-old plant growing in the field in July in full sun in Canby, Oreg.

DETAILED PLANT DESCRIPTION

The following is a detailed description of the new *Agastache* cultivar based on observations of 2-year-old specimens in early October growing in the field in Canby, Oreg. Canby is Zone 8 on the USDA Hardiness map. Temperatures range from a high of 95° F. in August to an average of 32° F. in January. Normal rainfall in Canby is 42.8 inches per year. The color descriptions are all based on The Royal Horticultural Society Colour Chart, 5$^{th}$ edition, 2007.

Plant:

*Form*.—Upright.
*Type*.—Herbaceous perennial.
*Cold hardiness*.—USDA Zone 5-10.
*Size*.—Grows to 53 cm wide and 64 cm tall to the top of the flowers.
*Vigor*.—Excellent.
*Branching*.—About 6 main stems from the base, these branch at every node.

*Stem*.—Square in cross section, grows to 6 mm wide and 24 cm tall to the first flower, pubescent, internodes range from 2 cm to 7 cm long, between Yellow Green 146B and Yellow Green 146C.

*Roots*.—White 155C, fibrous, plants root easily from stem tip cuttings.

Leaf:

*Type*.—Simple.

*Arrangement*.—Opposite.

*Shape*.—Ovate.

*Venation*.—Cross-venulate.

*Margins*.—Crenate.

*Apex*.—Acute.

*Base*.—Lanceolate.

*Blade size*.—Grows to 39 mm long and 23 mm wide.

*Surface texture*.—Pubescent on both sides.

*Petiole description*.—Grows to 13 mm long and 1 mm wide, pubescent, Yellow Green 145B.

*Leaf color*.—Top side closet to Yellow Green 137B including vein, bottom side closest to Yellow Green 146C with vein Yellow Green 148C.

*Fragrance*.—Aromatic.

Inflorescence:

*Type*.—Terminal spike with up to 11 whorls.

*Number of flowers*.—About 130 per spike.

*Size of inflorescence*.—Grows to 11 cm tall and 7 cm wide.

*Peduncle*.—Grows to 7 cm tall and 2 mm wide, pubescent, Yellow Green 145B.

*Pedicel*.—Grows to 2 mm long, pubescent, Yellow Green 146C.

*Bloom period*.—June through frost in Canby, Oreg.

Flower bud:

*Size*.—9.2 mm long and 4 mm wide at the widest point prior to opening.

*Description*.—Tubular.

*Surface texture*.—Pubescent.

*Color*.—Orange Red N34B.

Flower:

*Type*.—Zygomorphic.

*Shape*.—Bilabiate, tubular.

*Size*.—32 mm long and 7 mm wide.

*Corolla description*.—25 mm long and 7 mm wide; color both sides closest to Orange Red 35A; glabrous inside and pubescent outside, tube 25 mm long and 1 mm to 7 mm wide; 2 upper lobes joined 4 mm long and 3 mm wide, each oblong, tips obtuse, margin entire; three lower lobes, two spreading sideways and reflex, each 3.5 mm long and 3 mm wide, tip acute, margin entire; bottom lobe cupped, broadly obovate, notched at the tip, margin serrate, 6.5 mm wide and 5 mm deep.

*Calyx description*.—Campanulate, 7 mm long and 3 mm wide, pubescent outside and glabrous inside, 5 lobed, lobes ovate, 1.5 mm long, entire, acute, outside Yellow Green 144C tinted with Purple N77B near tip, inside Yellow Green 144C.

*Pistil description*.—32 mm long, ovary 1.5 mm long, Yellow Green 145C, style 25 mm long, White NN155D at bottom blending to Purple Violet N81B at top, stigma two-parted, 1 mm deep, Red Purple 71A.

*Stamen description*.—4 in number, paired and exerted, top two 9 mm long and bottom two 7 mm long, filaments Orange Red 32C, anthers 1 mm long, Red Purple 71A, pollen Yellow 3D.

*Fragrance*.—Aromatic.

*Lastingness*.—A spike blooms for about 4 weeks on the plant.

Fruit/seed: 4 nutlets, 1 mm long, ovoid, Black 202A.

Pests and diseases: The new cultivar is typical to the genus. No known resistances to pests or diseases. No problems have been found in Canby, Oreg.

I claim:

1. A new and distinct form of *Agastache* plant substantially as shown and described.

* * * * *

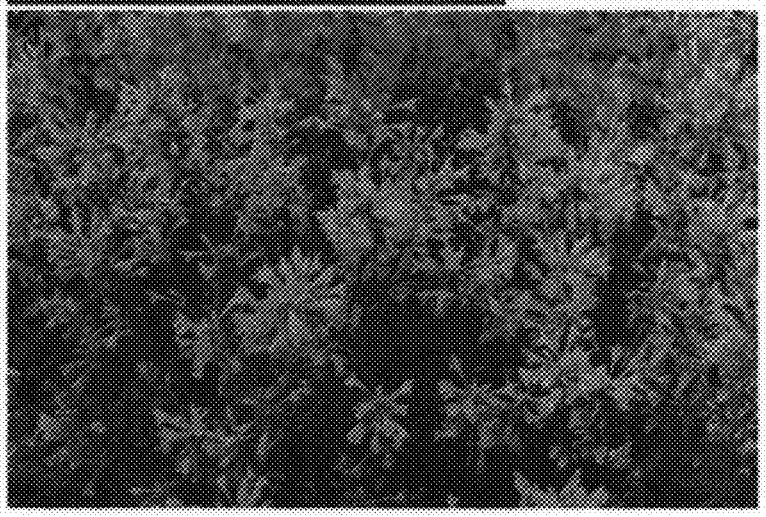

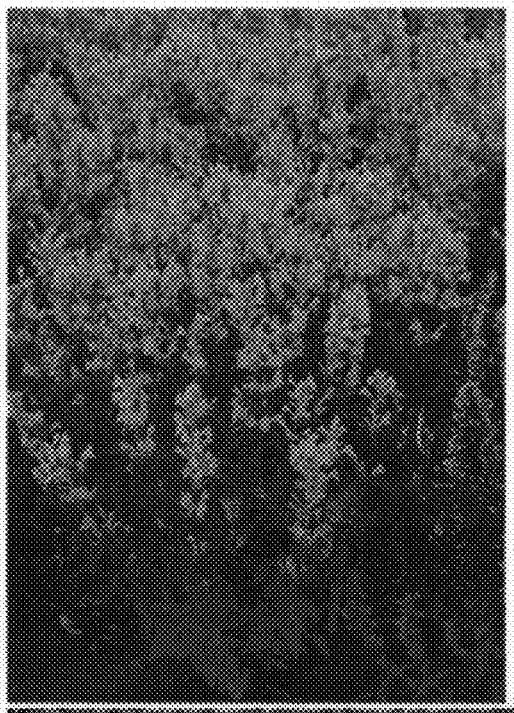
FIG. 1 Left
FIG. 2 Below